United States Patent [19]

Harris

[11] Patent Number: 4,521,536
[45] Date of Patent: Jun. 4, 1985

[54] PESTICIDAL NITROMETHYLENE DERIVATIVES

[75] Inventor: Martin Harris, Sittingbourne, England

[73] Assignee: Shell Oil Company, Houston, Tex.

[21] Appl. No.: 578,144

[22] Filed: Feb. 8, 1984

[30] Foreign Application Priority Data

Feb. 17, 1983 [GB] United Kingdom ............... 8304386
Apr. 26, 1983 [GB] United Kingdom ............... 8311358
Sep. 23, 1983 [GB] United Kingdom ............... 8325539

[51] Int. Cl.³ .................... C07D 279/04; A01N 43/86
[52] U.S. Cl. ........................................ 514/226; 544/54
[58] Field of Search ......................... 544/54; 424/246

[56] References Cited

U.S. PATENT DOCUMENTS 4,052,388 10/1977 Powell .................................. 544/54

*Primary Examiner*—John M. Ford

[57] ABSTRACT

Substituted 2-nitromethylene-tetrahydro-2H-1,3-thiazines of formula:

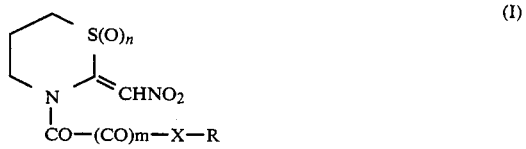

in which n is 0 or 1; m is 0 or 1; X is oxygen or sulphur; and R is alkyl, alkenyl or alkynyl optionally substituted by one or more of the same or different substituents selected from halogen atoms and hydroxy, thiol, acyloxy, acylthio, alkoxy, alkoxyalkoxy, haloalkoxy, and optionally substituted phenyl groups; have useful pesticidal properties.

3 Claims, No Drawings

PESTICIDAL NITROMETHYLENE DERIVATIVES

This invention relates to certain substituted 2-nitromethylene-tetrahydro-2H-1,3-thiazines, to a process for their preparation and to their use as pesticides, in particular against insect pests.

U.S. Pat No. 4,052,388 describes the compound 3-acetyl-2-nitromethylene-tetrahydro-2H-1,3-thiazine and its insecticidal properties. It has now been found that certain similar thiazine derivatives containing an ester or thioester group also exhibit interesting pesticidal activity.

Accordingly the invention provides substituted 2-nitromethylene-tetrahydro-2H-1,3-thiazines of the formula:

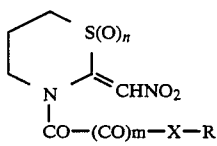
(I)

in which n is 0 or 1; m is 0 or 1; X is oxygen or sulphur; and R is alkyl, alkenyl or alkynyl optionally substituted by one or more of the same or different substituents selected from halogen atoms and hydroxy, thiol, acyloxy, acylthio, alkoxy, alkoxyalkoxy, haloalkoxy, and optionally substituted phenyl groups.

Unless otherwise stated, throughout this Specification any alkyl, alkenyl or alkynyl moiety preferably has up to 6, especially up to 4, carbon atoms.

Preferred substituents which may be present in an optionally substituted phenyl moiety include halogen atoms and alkyl, haloalkyl, alkoxy, haloalkoxy, cyano, nitro, amino and hydroxy groups. Especially preferred substituents are halogen atoms and C(1–4) alkyl, especially methyl, groups.

Preferred acyl groups are formyl groups and optionally substituted alkanoyl and benzoyl groups in which the preferred substituents for the benzoyl group are as given above for a phenyl group and the preferred substituents for the alkanoyl group are halogen atoms, alkoxy groups and phenyl groups.

Preferably R represents an alkyl, alkenyl or alkynyl group having up to 6, especially up to 4, carbon atoms optionally substituted by one or more of the same or different substituents selected from halogen atoms and hydroxy, formyloxy, alkanoyloxy or alkanoylthio having 1 to 4 carbon atoms in the alkyl moiety, alkoxy having 1 to 4 carbon atoms, alkoxyalkoxy having 1 or 2 carbon atoms in each alkoxy moiety, and phenyl groups.

Preferably X represents oxygen.
Preferably m is 0
Preferably n is 0.

Thus typical compounds of formula I are those in which n is 0 and the group —(CO)$_m$XR represents an alkoxy group of 1 to 6 carbon atoms optionally substituted by up to three chlorine atoms or by a phenyl group, for example, methoxy, ethoxy, isobutoxy, trichloroethoxy or benzyloxy; or an alkoxycarbonyl or alkynyloxy group, each of up to 6 carbon atoms, for example, ethoxycarbonyl or propynyloxy.

Further typical compounds of formula I are those in which n is 0 and the group —(CO)$_m$XR represents an alkoxy group of 1 to 6 carbon atoms substituted by up to three bromine atoms or by a hydroxy or an acyloxy group of up to 6 carbon atoms, for example, bromoethoxy, hydroxyethoxy, formyloxyethoxy or acetoxyethoxy.

It will be appreciated that the compounds of formula I are capable of existing in different geometrically isomeric forms. The invention includes both the individual isomers and mixtures of such isomers.

The invention also includes a process for the preparation of the substituted 2-nitromethylene-tetrahydro-2H-1,3-thiazines of formula I which comprises reacting the compound of the formula:

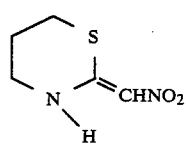
(II)

with a halo compound of formula:
R—X—(CO)$_m$—CO—Hal (III)

in which R, X and m are as defined in relation to formula I and Hal represents a halogen, preferably chlorine, atom, in the presence of a base, to give a compound of the formula I in which n is 0; and if desired, oxidising this compound to the corresponding compound in which n is 1. The base is preferably an organic base such as a tertiary amine, for example a trialkylamine, triethylamine being particularly preferred. The reaction is preferably carried out at a temperature of 0° C. or below, for example, at a temperature from −60° C. to 0° C., preferably −30° C. to −10° C. The reaction is suitably carried out in an organic solvent, for example, a chlorinated hydrocarbon such as dichloromethane, or an amide such as dimethylformamide.

The compounds of formula I in which n is 1 may be prepared by oxidising the corresponding derivative in which n is 0. This may be carried out using conventional oxidising agents, for example peracids such as m-chloroperbenzoic acid, or potassium hydrogen persulphate. Conveniently the derivative to be oxidised is dissolved in a suitable solvent, for example a chlorinated hydrocarbon solvent such as chloroform or dichloromethane, or a liquid alkanol such as ethanol.

It is also possible to prepare compounds according to formula I from other compounds according to formula I, which in turn may have been prepared by N-acylation of the compound according to formula II. For example, the compounds wherein R contains a hydroxy, thiol(-mercapto), acyloxy or acylthio group may be prepared from compounds wherein R contains a halogen, especially bromine, atom by reaction with a corresponding acyloxy or acylthio salt, and optional hydrolysis.

As mentioned above, the substituted 2-nitromethylene-tetrahydro-2H-1,3-thiazines of the invention are of interest as pesticides particularly against insect pests. They exhibit activity against such pests as the larval caterpillar or worm forms of insects, for example, of the genus Spodoptera and of the genus Heliothis. They are particularly useful for combatting pests found in rice crops. For certain applications, the combined physical and biological properties of the compounds of the invention are more advantageous than those of the known insecticide 3-acetyl-2-nitromethylene-tetrahydro-2H-1,3-thiazine.

Accordingly the invention includes pesticidal compositions comprising a substituted 2-nitromethylene-tetrahydro-2H-1,3-thiazine of the invention together with a carrier.

Such a composition may contain a single compound or a mixture of several compounds of the invention. It is also envisaged that different isomers or mixtures of isomers may have different levels or spectra of activity and thus compositions may comprise individual isomers or mixture of isomers. The invention further provides a method of combating pests, particularly insect pests at a locus, which comprises applying to the locus a pesticidally effective amount of a compound or composition according to the present invention. An especially preferred locus is a paddy field bearing rice crops.

A carrier in a composition according to the invention is any material with which the active ingredient is formulated to facilitate application to the locus to be treated which may for example be a plant, seed or soil, or to facilitate storage, transport or handling. A carrier may be a solid or a liquid, including a material which is normally gaseous but which has been compressed to form a liquid, and any of the carriers normally used in formulating pesticidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montomorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of active ingredient. Granules are usually prepared to have a size between 10 and 100 BS mesh (1.676–0.152 M), and may be manufactured by agglomeration or impregnation techniques. Generally, granules will contain ½–75% w active ingredient and 0–10% w of additives such as stabilisers, surfactants, slow release modifiers and binding agents. The so-called "dry flowable powders" consists of relatively small granules having a relatively high concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

A composition of the invention may also contain other ingredients, for example, one or more other compounds possessing pesticidal, herbicidal or fungicidal properties, or attractants, for example pheromones or food ingredients, for use in baits and trap formulations.

It has also been found that the thermal stability of the compounds and compositions of the invention may be improved by the addition of stabilizing amounts, usually 10–100% w based on the compound, of certain organo nitrogen compounds such as urea, dialkylureas, thiourea or guanidine salts or alkali metal salts of weak acids such as bicarbonates, acetates or benzoates.

The invention is illustrated further in the following Examples.

EXAMPLE 1

3-Methoxycarbonyl-2-nitromethylene-tetrahydro-2H-1,3-thiazine

Methoxycarbonyl chloride (5.7 g) in dichloromethane (60 ml) was added dropwise over a period of 30 minutes to a solution of 2-nitromethylene-tetrahydro-2H-1,3-thiazine (6.4 g) and triethylamine (10.4 ml) in dichloromethane (60 ml) at $-20°$ C. under nitrogen. The reaction mixture was allowed to warm to ambient temperature over a period of 60 minutes and was then washed with 2% hydrochloric acid. The organic phase was dried (MgSO$_4$) and the solvent was removed under reduced pressure. The residue was triturated with ethyl acetate to yield the required product as a crystalline solid m.p. 93°–95° C.

Analysis: Calculated for $C_7H_{10}O_4N_2S$: C 38.5%; H 4.6%; N 12.8%, Found: C 38.4%; H 4.6%; N 12.8%

EXAMPLE 2

3-(2-Bromoethoxycarbonyl)-2-nitromethylene-tetrahydro-2H-1,3-thiazine

To a mixture of 12.8 g 2-nitromethylene-tetrahydro-2H-1,3-thiazine, 21 ml triethylamine and 120 ml dichloro methane was added dropwise over 75 minutes, at $-30°$ C. under nitrogen, a solution of 18 g 2-bromoethyl chloroformate in 100 ml dichloro methane. The reaction mixture was allowed to warm to 0° C., over 30 minutes, with stirring, and then washed with 2% hydrochloric acid. The organic phase was separated off and dried (MgSO$_4$), and the solvent was evaporated off. The solid material (27.2 g) was purified on a silica gel column using a 199:1 mixture (vol/vol) of dichloro methane and methanol, to yield 19.7 g of crystals, having a melting point of 79°–81° C.

| Analysis | C | H | N |
|---|---|---|---|
| Calculated for $C_8H_{11}N_2O_4SBr$ | 30.9%; | 3.5%; | 9.0% |
| Found | 30.7%; | 3.5%; | 8.9% |

EXAMPLE 3

3-(2-Formyloxyethoxycarbonyl)-2-nitromethylene-tetrahydro-2H-1,3-thiazine.

The compound of Examples 2 (8 g) was dissolved in 35 ml hexamethylphosphoramide (HMPA), and added to 11 g sodium formate in 45 ml HMPA, at 0° C. under nitrogen.

The mixture was stirred at 20° for 38 hours then poured into diethyl ether, and washed with brine which was then washed back with diethyl ether. The combined organic phases were dried and evaporated to afford an oil (10 g) which was purified by column chromatography on silica to afford the title compound as a yellow crystalline solid (3.8 g) and recovered starting material (0.7 g).

Melting point 66°–69° C.

| Analysis | C | H | N |
|---|---|---|---|
| Calculated for $C_9H_{12}N_2O_6S$ | 39.1% | 4.4% | 10.1% |
| Found | 39.2% | 4.2% | 10.0% |

EXAMPLE 4

3-(2-Hydroxyethoxycarbonyl)-2-nitromethylene-tetrahydro-2H-1,3-thiazine

The compound of Example 3 (2 g) was passed down a column of neutral alumina (200 g) using a dichloro methane/methanol mixture (95/5, v/v) as eluent at a flow rate of approximately 35 ml per minute. The eluted material was concentrated and purified by column chromatography on silica to afford the title compound (1.1 g) and recovered starting material (600 g). Melting point of the product was 59°–62° C.

| Analysis | C | H | N |
|---|---|---|---|
| Calculated for $C_8H_{12}N_2O_5S$ | 38.7% | 4.8% | 11.3% |
| Found | 39.0% | 5.2% | 10.5% |

EXAMPLES 5–28

Further compounds were prepared using procedures similar to those of the previous Examples. These compounds are identified together with their melting points and analyses in Table A.

TABLE A

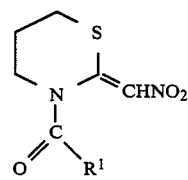

| Example | R$^1$ | m.p. °C. | Analysis | C % | H % | N % |
|---|---|---|---|---|---|---|
| 5 | —OCH$_2$C≡CH | 58–60 | Calc. | 44.6 | 4.1 | 11.6 |
|   |   |   | Found | 44.3 | 4.2 | 11.5 |
| 6 | —COOC$_2$H$_5$ | 99–100 | Calc. | 41.5 | 4.6 | 10.8 |
|   |   |   | Found | 41.5 | 4.8 | 10.7 |
| 7 | —OC$_2$H$_5$ | oil | Calc. | 41.4 | 5.2 | 12.1 |
|   |   |   | Found | 41.4 | 5.4 | 11.9 |
| 8 | —OCH$_2$CH(CH$_3$)$_2$ | oil | Calc. | 46.2 | 6.2 | 10.8 |
|   |   |   | Found | 46.2 | 6.4 | 10.7 |
| 9 | —OCH$_2$CCl$_3$ | 103–105 | Calc. | 28.6 | 2.7 | 8.4 |
|   |   |   | Found | 28.7 | 2.7 | 8.3 |
| 10 | —OCH$_2$C$_6$H$_5$ | 78–80 | Calc. | 53.1 | 4.8 | 9.5 |
|   |   |   | Found | 52.9 | 4.8 | 9.3 |

TABLE A-continued

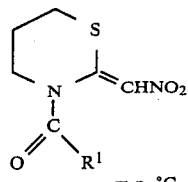

| Example | R¹ | m.p. °C. | Analysis | C % | H % | N % |
|---|---|---|---|---|---|---|
| 11 | —OCH₂CHCl₂ | oil | Calc. | 31.9 | 3.3 | 9.3 |
| | | | Found | 31.3 | 3.1 | 8.9 |
| 12 | —OCH₂CH₂OCO.CH₃ | 58–62 | Calc. | 41.4 | 4.8 | 9.7 |
| | | | Found | 41.5 | 5.0 | 9.6 |
| 13 | —O.(CH₂)₂I | 52–54 | Calc. | 26.8 | 3.1 | 7.8 |
| | | | Found | 27.2 | 3.1 | 7.8 |
| 14 | —O.(CH₂)₃I | oil | Calc. | 29.0 | 3.5 | 7.5 |
| | | | Found | 29.6 | 3.6 | 7.4 |
| 15 | —O.(CH₂)₃Cl | oil | Calc. | 38.6 | 4.8 | 9.9 |
| | | | Found | 38.6 | 4.6 | 10.0 |
| 16 | —O.(CH₂)₄I | oil | Calc. | 31.1 | 3.9 | 7.3 |
| | | | Found | 31.3 | 4.0 | 7.4 |
| 17 | —O.(CH₂)₄Cl | oil | Calc. | 40.7 | 5.1 | 9.5 |
| | | | Found | 41.5 | 5.1 | 9.3 |
| 18 | —S.C₂H₅ | oil | Calc. | 38.7 | 4.8 | 11.3 |
| | | | Found | 38.7 | 5.0 | 10.6 |
| 19 | —O.(CH₂)₂O.CH(CH₃)OC₂H₅ | oil | Calc. | 45.0 | 6.3 | 8.8 |
| | | | Found | 45.0 | 6.2 | 8.7 |
| 20 | —S.(CH₂)₂CH₃ | oil | Calc. | 41.2 | 5.3 | 10.7 |
| | | | Found | 41.7 | 5.4 | 10.7 |
| 21 | —O.(CH₂)₃O.CHO | oil | Calc. | 41.4 | 4.8 | 9.7 |
| | | | Found | 41.6 | 4.9 | 9.2 |
| 22 | —O.(CH₂)₃OH | oil | Calc. | 41.2 | 5.3 | 10.7 |
| | | | Found | 40.7 | 5.5 | 10.4 |
| 23 | —O.(CH₂)₃O.CO.CH₃ | 55 | Calc. | 43.4 | 5.3 | 9.2 |
| | | | Found | 43.3 | 5.3 | 9.2 |
| 24 | —O.(CH₂)₄O.CHO | oil | Calc. | 43.4 | 5.3 | 9.2 |
| | | | Found | 43.4 | 5.3 | 9.2 |
| 25 | —O.(CH₂)₄O.CO.CH₃ | oil | Calc. | 45.3 | 5.7 | 8.8 |
| | | | Found | 45.3 | 5.7 | 8.2 |
| 26 | —O.(CH₂)₄OH | oil | Calc. | 43.5 | 5.8 | 10.1 |
| | | | Found | 42.8 | 6.1 | 9.8 |
| 27 | —O.CH₂.CH═CH₂ | oil | Calc. | 44.3 | 4.9 | 11.5 |
| | | | Found | 44.3 | 5.0 | 11.4 |
| 28 | —O.(CH₂)₂S.CO.CH₃ | 72–73 | Calc. | 38.9 | 4.8 | 8.8 |
| | | | Found | 39.2 | 4.6 | 9.2 |

EXAMPLE 29

Preparation of the S-oxide of the compound of Example 2 m-chloroperbenzoic acid (2.0 g) dissolved in dichloromethane (100 mls) was added dropwise over 30 minutes to a stirred solution of the compound of Example 2 (2.0 g) in dichloromethane (150 mls) at −15° C. The mixture was allowed to warm to room temperature and stirred for 2 hours. Sodium carbonate (6 g) was added, and the mixture stirred for a further hour, filtered, and the solvent removed under reduced pressure. The residue was purified by column chromatography over silica to give 1.0 g of the desired product as an oil.

| Elemental Analysis | C | H | N |
|---|---|---|---|
| Calculated for C₇H₁₂NO₃Br | 29.6 | 3.5 | 8.1 |
| Found | 29.4 | 3.4 | 8.6 |

EXAMPLE 30

Pesticidal Activity

The pesticidal activity of the compounds of the invention was assessed against the following insect pests.
*Spodoptera littoralis* (S.l.)
*Aedes aegypti* (A.a.)
*Musca domestica* (M.d.)
*Aphis fabae* (A.f.)

The test methods employed for each species appear below; in each test, unless otherwise stated, a 0.2% solution or suspension of each test compound in 16.7% acetone in water containing 0.04% Triton X-100 (Trade Mark) was sprayed onto the test species; controls were sprayed with a control solution of water, acetone and Triton X-100 (Trade Mark) in the same proportions. These tests were all conducted under normal insectary conditions 23° C.±2° C. (fluctuating light and humidity).

(i) *Spodoptera littoralis* (S.l.)

Second instar larvae were used in the tests. Each test solution and the control solution was sprayed onto a separate petri dish containing a nutrious diet on which the *Spodoptera littoralis* larvae had been reared.

When the spray deposit had dried each dish was infested with 10 2nd instar larvae. Mortality assessments were made 1 and 7 days after spraying and the percentage mortality calculated.

(ii) *Aedes aegypti* (A.a.)

Early 4th instar larvae were used in the tests. Test solutions were made up to 3 ppm of active ingredient in water containing 0.04% Triton X-100 (Trade Mark); acetone was initially present to aid solution, but was subsequently allowed to evaporate off.

Ten early 4th instar larvae were placed in 100 ml of the test solution. After 48 hours, larval mortality (as a percentage) was recorded.

Any surviving larvae were then fed with a small quantity of animal feed pellets and the final percentage mortality of adults and pupae made when all the larvae had either pupated and turned into adults, or died.

(iii) *Musca domestica* (M.d.)

Batches of ten 2 to 3 day old milk-fed adult female houseflies (*Musca domestica*) anaesthetized using carbon dioxide were placed on petri dishes lined with filter paper. The dishes were sprayed with the test formulations using a spray machine operating on a logarithmic dilution principle. The flies were subsequently retained in the petri dishes and were fed with a dilute milk solution which was dripped down the side of the petri dish and absorbed onto the filter paper. Mortality was assessed after 24 hours.

(iv) *Aphis fabae* (A.f.)

Tests were carried out on adult black bean aphids (*Aphis fabae*). Pairs of broad bean leaves on filter paper in petri dishes were sprayed side by side with uncounted quantities of aphids in small gauze-covered containers. After passing through the spray the aphids were tipped onto the leaves and lids were placed on the petri dishes. Mortality was assessed after 24 hours.

The results of these tests are shown in Table B in which the test species are identified by the initials noted above and the activity of each compound is expressed in terms of the percentage mortality:
A: denotes 90–100% mortality
B: denotes 50–80% mortality
C: denotes 0–40% mortality.

TABLE B

| Compound of Example No. | Insecticidal Activity | | | | | |
|---|---|---|---|---|---|---|
| | S.l. | | A.a. | | M.d. | A.f. |
| | 1 day | 7 days | 2 days | Final | | |
| 1 | A | A | B | A | A | A |
| 2 | B | A | A | A | A | B |
| 3 | A | A | A | A | A | A |
| 4 | C | C | A | A | A | A |
| 5 | B | A | A | A | A | A |
| 6 | A | A | A | A | A | A |
| 7 | A | A | A | A | A | A |
| 8 | B | A | A | A | A | A |
| 9 | B | A | A | A | A | A |
| 10 | A | A | A | A | A | A |
| 11 | | | | | | |
| 12 | A | A | A | A | A | A |
| 13 | C | A | B | A | A | A |
| 14 | C | C | B | A | — | C |
| 15 | C | A | C | A | A | C |
| 16 | C | A | C | A | A | B |
| 17 | B | A | C | A | A | A |
| 18 | A | A | A | A | A | C |
| 19 | B | A | C | B | B | A |
| 20 | B | A | B | A | A | A |
| 21 | A | A | B | A | A | C |
| 22 | A | A | C | A | A | B |
| 23 | C | A | C | A | A | B |
| 24 | C | B | C | B | A | B |
| 25 | C | C | C | B | A | C |
| 26 | C | C | C | A | A | C |
| 27 | B | A | A | A | A | A |
| 28 | A | A | A | A | A | A |

TABLE B-continued

| Compound of Example No. | Insecticidal Activity | | | | | |
|---|---|---|---|---|---|---|
| | S.l. | | A.a. | | M.d. | A.f. |
| | 1 day | 7 days | 2 days | Final | | |
| 29 | B | B | A | A | A | B |

EXAMPLE 31

Determination of Toxicity Index

The toxicities of compounds according to the invention relative to a standard insecticide, Parathion, against corn earworm larvae (*Heliothis zea*) were tested by spraying a broad bean plant with aqueous dilutions of an acetone solution of test compound containing an emulsifier. Immediately after spraying, 5 larvae were transferred to the plant and held for 44–46 hours, at which time the dead and moribund larvae were counted. The tests were conducted employing several different dosage rates for each test compound.

In each instance, the toxicity of the compound of the invention was compared to that of a standard pesticide, Parathion, the relative toxicity then being expressed in terms of the relationship between the amount of compound of the invention and the amount of the standard pesticide required to produce 50% mortality of the test insect. The standard pesticide is given an arbitrary Toxicity Index of 100. Thus a test compound having a Toxicity Index of 200 would be twice as active, as the standard pesticide. The Toxicity Indices measured are given in Table C.

TABLE C

| Compound of Example No. | Toxicity Index relative to Parathion = 100 |
|---|---|
| 1 | 638 |
| 2 | 1000 |
| 3 | 2000 |
| 4 | 3000 |
| 5 | 1485 |
| 9 | 1856 |
| 10 | 1000 |
| 11 | 1000 |
| 12 | 1000 |

I claim:
1. A compound of the formula

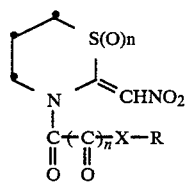

wherein n is zero or one, m is zero or one, X is oxygen or sulfur and R is alkyl, alkenyl or alkynyl of up to six carbon atoms optionally substituted by one or more halogen, or by hydroxy; mercapto; formyloxy; thioformyl; or alkanoyloxy, alkanoylthio, alkoxy, alkylthio, alkoxyalkoxy, or haloalkoxy wherein the alkyl moiety contains from one to four carbon atoms; or phenyl optionally substituted by one or more of halogen and alkyl of from one to four carbon atoms.

2. A method for protecting a locus from unwanted insects, that comprises applying to the locus to be protected an effective dosage of a compound of claim 1.

3. An insecticidal composition, that comprises an effective amount of a compound of claim 1 together with an inert carrier, optionally a surface-active agent.

* * * * *